United States Patent

Slusarchyk et al.

[11] 4,039,534
[45] Aug. 2, 1977

[54] 4-THIO SUBSTITUTED-Δ²-CEPHALOSPORIN INTERMEDIATES

[75] Inventors: William A. Slusarchyk, Belle Mead; Christopher M. Cimarusti, Hamilton, both of N.J.

[73] Assignee: E. R. Squibb & Sons, Inc., Princeton, N.J.

[21] Appl. No.: 632,618

[22] Filed: Nov. 17, 1975

[51] Int. Cl.² .......................................... C07D 501/18
[52] U.S. Cl. ...................................... 544/17; 424/246
[58] Field of Search ................................ 260/243 C

[56] References Cited

U.S. PATENT DOCUMENTS

| 3,849,408 | 11/1974 | Dolfini | 260/243 C |
|---|---|---|---|
| 3,941,779 | 3/1976 | Slusarchyk et al. | 260/243 C |

*Primary Examiner*—Nicholas S. Rizzo
*Assistant Examiner*—Jose Tovar
*Attorney, Agent, or Firm*—Lawrence S. Levinson; Merle J. Smith; Stephen B. Davis

[57] ABSTRACT

Cephalosporin intermediates of the formulas

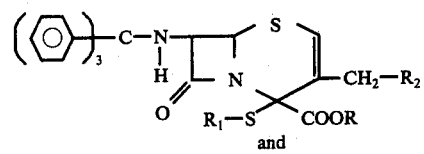

and

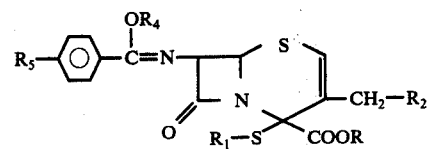

wherein R is lower alkyl, 2,2,2-trichloroethyl, diphenylmethyl, p-methoxybenzyl, or p-nitrobenzyl; $R_1$ is lower alkyl or phenyl; $R_2$ is hydrogen or acetoxy; $R_4$ is methyl or ethyl; and $R_5$ is hydrogen, methyl, or methoxy; are disclosed. Methods of reacting these intermediates to prepare antibacterially active cephalosporins are disclosed.

4 Claims, No Drawings

4-THIO SUBSTITUTED-Δ²-CEPHALOSPORIN INTERMEDIATES

BACKGROUND OF THE INVENTION

4-Substituted-Δ²-cephalosporins are disclosed by Dolfini in U.S. Pat. No. 3,849,408. Also, various 4-thio substituted-3-acetoxy or desacetoxy-Δ²-cephalosporins and methods of their preparation are disclosed in Slusarchyk et al. in German Offenlegungsschrift No. 2,453,601, (May 15, 1975).

SUMMARY OF THE INVENTION

This invention relates to new 4-thio substituted cephalosporin intermediates of the formulas

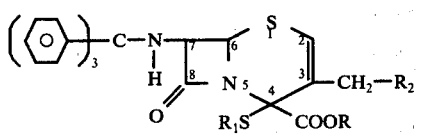

and

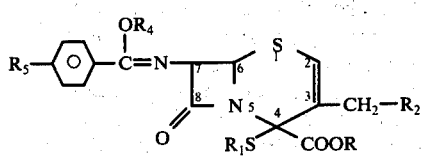

wherein R is lower alkyl, 2,2,2-trichloroethyl, diphenylmethyl, p-methoxybenzyl, or p-nitrobenzyl; $R_1$ is lower alkyl or phenyl; $R_2$ is hydrogen or acetoxy; $R_4$ is methyl or ethyl; and $R_5$ is hydrogen, methyl or methoxy.

Also disclosed are methods of preparing these intermediates and of reacting these intermediates to prepare cephalosporins possessing antibacterial activity.

The intermediates of formulas I and II can be reacted as set forth below to yield the compounds

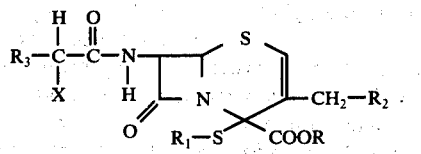

wherein R, $R_1$ and $R_2$ are as defined above, $R_3$ represents certain heterocyclic groups, lower alkyl, cycloalkyl, cycloalkenyl, cycloalkadienyl, phenyl, phenoxy, phenyl-lower alkyl, or substituted phenyl, and X is hydrogen, amino or hydroxy provided that X is amino or hydroxy only when $R_3$ is phenyl, substituted phenyl, or cycloalkadienyl. The compounds of formula III prepared by other methods are disclosed in German Offenlegungsschrift No. 2,453,601.

DETAILED DESCRIPTION

The various groups represented by the symbols have the meaning defined below and these definitions are retained throughout this specification.

The term "lower alkyl" is intended to include straight or branched chain hydrocarbon groups containing 1 to 4 carbons, i.e. methyl, ethyl, n-propyl, i-propyl, t-butyl, etc. The term "phenyl-lower alkyl" includes such lower alkyl groups attached to a phenyl with benzyl and phenethyl being preferred. The "lower alkoxy" groups include such lower alkyl groups attached to an oxygen, i.e. methoxy, ethoxy, etc.

"Cycloalkyl" refers to groups having 3 to 7 carbons in the ring, i.e. cyclopropyl, cyclobutyl, cyclopentyl, cyclohexyl, and cycloheptyl. The term "cycloalkenyl" also represents ring having 3 to 7 carbon atoms with one double bond, i.e., cyclobutenyl, cyclopentenyl, cyclohexenyl, etc. The term "cycloalkadienyl" represents a ring having 6 or 7 carbons with two double bonds located at various positions such as 1,4-cyclohexadienyl which is preferred.

The "substituted phenyl" groups include one or two simple substituents such as halogen (preferably Cl or Br), lower alkyl, or lower alkoxy, i.e. 2-, 3-, or 4-chlorophenyl, 2-, 3- or 4-bromophenyl, 3,5-dichlorophenyl, 2-, 3- or 4-methylphenyl, 2-, 3- or 4-methoxyphenyl, etc.

The heterocyclics represented by $R_3$ are thienyl, furyl, pyrryl, pyridyl, thiazolyl, isothiazolyl, oxazolyl, isoxazolyl, thiadiazolyl, and tetrazolyl. They are attached at any available carbon atom as for example 2- or 3-thienyl, 2- or 3-furyl, 2- or 3-pyrryl, 2-, 3- or 4-pyridyl, 2- or 5-thiazolyl, 3- or 5-isothiazolyl, 2- or 5-oxazolyl, 3- or 5-isoxazolyl, 3- or 5-(1,2,4-thiadiazolyl), etc. Also included within the meaning of $R_3$ are such heterocyclics having a halogen (preferably Cl or Br) or a lower alkyl (preferably methyl or ethyl) substituent, i.e. 5-(1-methyltetrazolyl), 2-(5-chlorothienyl), 2-(4-chloropyrryl), etc.

The novel intermediates of formula I are prepared by reacting a compound of the formula

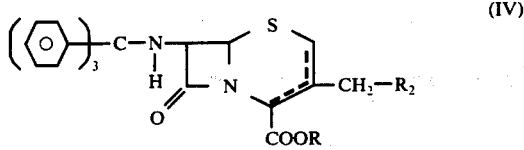

wherein R and $R_2$ are as defined above and the dashed line indicates that the double bond may be in either the 2- or 3-position, with one to two equivalents of a strong organometallic base such as potassium t-butoxide, n-butyl lithium, triphenylmethyl lithium, lithium N-cyclohexylisopropyl amide, lithium diethylamide or lithium hexamethyldisilazane, followed by a thiolating agent. The thiolating agent can be any of a varied group of agents known to introduce a substituted sulfur such as a compound of the formula $$R_1-S-Y \qquad (V)$$

wherein Y is halogen (preferably Cl or Br), lower alkoxycarbonyl (preferably methoxycarbonyl), or a sulfonic acid ester, e.g. $-SO_2-Z$ wherein Z is lower alkyl, phenyl, or substituted phenyl; or a disulfide thiolating agent of the formula $$(R_1-S)_2 \qquad (VI)$$

wherein $R_1$ is as defined above. About one equivalent or more of the thiolating agent is used. This reaction is performed in an inert organic solvent such as dimethoxyethane, dimethylformamide, tetrahydrofuran, dimethylsulfoxide, dioxane, or the like, at a temperature range of from about −70° to about 30° C for from several minutes to several hours. The reaction is best carried out under an inert atmosphere, e.g. argon or nitrogen.

The resulting intermediates of formula I can then be hydrolyzed with an acid such as p-toluene-sulfonic acid, hydrochloric acid, sulfuric acid or perchloric acid to remove the triphenylmethyl protecting group and yield

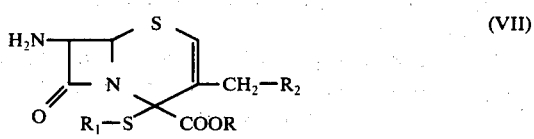
(VII)

This hydrolysis reaction is performed in an inert organic solvent such as acetone, dioxane, tetrahydrofuran, dimethoxyethane, ethyl acetate, chloroform, dichloromethane, or the like, at a temperature of from about $-30°$ to $30°$ C for from about 15 minutes to about 16 hours. The amine of formula VII can be isolated as an acid salt or as the free base, i.e., by treating the acid salt with sodium bicarbonate.

The amine of formula VII is then acylated by treatment with 1 to 2 equivalents of an acid halide (preferably chloride or bromide) of the formula

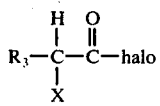

or acid anhydride of the formula

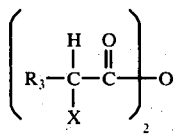

or mixed anhydride in the presence of 1 to 2 equivalents of a base such as triethylamine, pyridine, or N,N-diisopropylethylamine. This acylating reaction is performed in the presence of an inert organic solvent such as ethyl acetate, acetone, CHCl$_3$, CH$_2$Cl$_2$, acetonitrile, dioxane, dimethoxyethane, or tetrahydrofuran at a temperature of from about $-40°$ to about $30°$ C for from about 15 minutes to about 16 hours.

When X is amino or hydroxy, it is preferred to employ a protected acylating agent, for example a protected hydroxy acyl halide such as

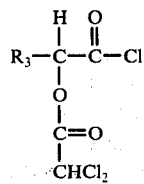

or a protected amino acid anhydride such as

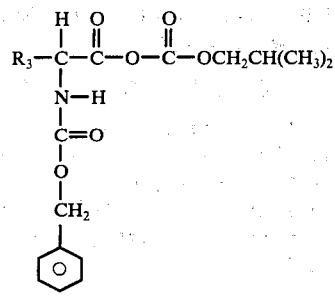

or

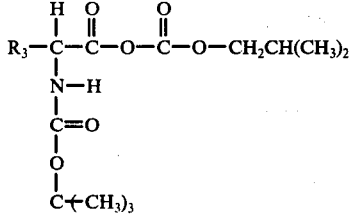

wherein R$_3$ is phenyl, substituted phenyl or cycloalkadienyl. The hydroxy protecting group can be removed by treating the protected compound with aqueous sodium carbonate or aqueous sodium hydroxide at a pH of about 9.5 for about 1 hour. The amino protecting groups can be removed by treatment with trifluoroacetic acid.

The novel intermediates of formula II are prepared by reacting a compound of the formula

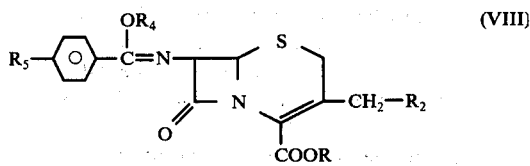
(VIII)

wherein R$_4$ is methyl or ethyl and R$_5$ is hydrogen, methyl or methoxy, with a thiolating agent of either formula V or VI in the presence of any of the lithium bases listed above in an inert organic solvent such as dimethoxyethane, dimethylformamide, tetrahydrofuran, dimethylsulfoxide, dioxane, or the like, at a temperature of from about $-70°$ to $30°$ C for from about several minutes to about 2 hours.

The resulting intermediates of formula II are then acylated by reacting with an acyl halide (preferably chloride or bromide) of the formula

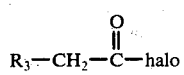

in the presence of water to yield the compound of formula III wherein X is hydrogen. This acylation reaction can be performed in various organic inert solvents such as CHCl$_3$, CH$_2$Cl$_2$, acetone, ethyl acetate, dioxane, dimethoxyethane, tetrahydrofuran, acetonitrile, or the like, at a temperature of from about $-30°$ to $30°$ C for from about 15 minutes to about 24 hours.

The esters of formula III wherein R is lower alkyl other than t-butyl, 2,2,2-trichloroethyl, or p-nitrobenzyl are particularly adapted to function as intermediates in preparing the free acid compounds of the formula

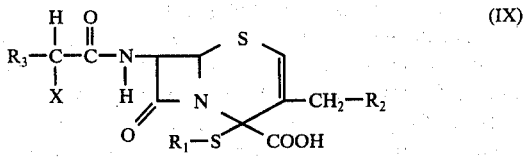

when R is lower alkyl other than t-butyl, or 2,2,2-trichloroethyl, this reaction is performed by treating the ester with one equivalent of base such as sodium hydroxide, potassium hydroxide, or lithium hydroxide in an aqueous and organic solvent system at a temperature of from about −30° to 30° C for from about 10 minutes to about 4 hours. Suitable organic solvents include dioxane, dimethoxyethane, tetrahydrofuran, dimethylformamide, acetonitrile and acetone. This reaction is preferably performed under an inert atmosphere. When R is p-nitrobenzyl, this reaction is performed by treating the ester with sodium dithionite in an aqueous acetonitrile or dioxane solution at a pH greater than 7.5.

The resulting esters of formula III wherein the ester is t-butyl, diphenylmethyl, or p-methoxybenzyl are particularly adapted to function as intermediates in the preparation of cephalosporins of the formula

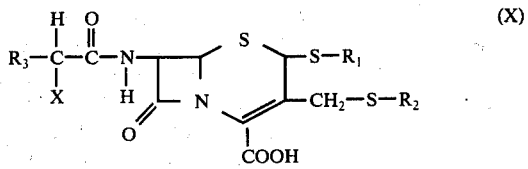

wherein $R_1$, $R_2$, $R_3$ and X are as defined above. This rearrangement reaction is performed by treating the ester with a strong, preferably anhydrous, acid. Such strong acids include halogenated fatty acids such as trifluoroacetic acid, hydrohalic acids such as hydrochloric acid, arylsulfonic acids such as benzene- or toluenesulfonic acid. The reaction medium is preferably an inert organic solvent such as nitromethane, dimethoxyethane, dioxane, chloroform, methylene chloride or the like. Trifluoroacetic acid is the preferred strong acid since it can, in addition, serve as the reaction medium.

The $\Delta^2$- or $\Delta^3$-cephalosporin esters of formula IV are prepared as a mixture by reacting an ester of the formula

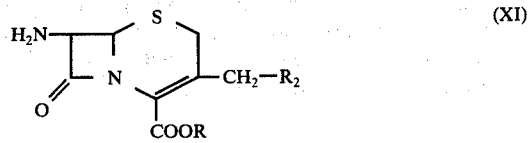

with triphenylmethyl chloride in the presence of triethylamine in an inert solvent such as $CH_2Cl_2$. The esters of formula VIII can be prepared by reacting an ortho ester of the formula

with the ester of formula XI in an inert solvent such as benzene, toluene, xylene, dimethoxyethane, dimethylformamide, dimethylacetamide, dimethylsulfoxide, acetonitrile, etc., at a temperature in the range 0° to 140° C. for a period of about 1 hour to 48 hours depending upon the temperature and solvent. Preferably a catalytic (trace) amount of acid catalyst like p-toluenesulfonic acid, hydrochloric acid, sulfuric acid or the like is present.

Additional process details are provided in the representative examples.

The acid compounds of formula IX and formula X are useful against gram-positive bacteria, such as *Staphylococcus aureus* and *Streptococcus pyogenes*. These compounds may be used to combat infections due to organisms such as those named above, and in general may be formulated and administered in a manner similar to cephalothin and other cephalosporins. For example, these compounds of formula IX and formula X or a physiologically acceptable salt thereof may be incorporated in an oral dosage form such as tablets, capsules, or elixirs, or in an injectable form in a sterile aqueous vehicle prepared according to conventional pharmaceutical practice.

The following examples represent preferred embodiments of this invention. All temperatures are on the centigrade scale.

EXAMPLE 1

3-Methyl-4-methylthio-7-phenylacetamido-$\Delta^2$-cephem-4-carboxylic acid a. 3-Methyl-7-triphenylmethylamino-$\Delta^3$-cephem-4-carboxylic acid, 2,2,2-trichloroethyl ester and corresponding $\Delta^2$-cephem isomer A mixture of 7-amino desacetoxycephalosporanic acid 2,2,2-trichloroethyl ester (0.039 mol.), triphenylmethyl chloride (0.039 mol.), and triethylamine (0.039 mol.) in 150 ml. of dry $CH_2Cl_2$ is stirred at 25° under nitrogen for 4 hours. The mixture is washed with water, dried ($Na_2SO_4$), and evaporated in vacuo to give the desired product as a residue (27.6 g.). Purification of this residue by dry column chromatography on four 2 × 24 inch columns using $CHCl_3$ provides, from inches 8 to 20, the desired product (18.9 g.) as a mixture of $\Delta^2$ and $\Delta^3$-cephem isomers.

b. 3-Methyl-4-methylthio-7-triphenylmethylamino-$\Delta^2$-cephem-4-carboxylic acid, 2,2,2-trichloroethyl ester To a stirred solution of the product from part (a) (31.9 g., 0.0545 mol.) in 200 ml. of dry dimethoxyethane at −10° under $N_2$ is added potassium t-butoxide (6.14 g., 0.0545 mol.). The mixture is stirred for 3 minutes, and then methyl methanethiolsulfonate (6.87 g., 0.0545 mol.) in 30 ml. of dimethoxyethane is added dropwise but rapidly. Stirring is continued at −10° for 1 hour, and the dark red-brown mixture is poured into pH 6.6 butter-ice-$CHCl_3$. Repeated extraction with $CHCl_3$ provides after drying ($Na_2SO_4$), and evaporation of the $CHCl_3$ in vacuo the desired product as a foam (33.5 g., 80% pure as determined by pmr spectroscopy), having pmr ($DCCl_3$) $\tau$ 8.07 (3H,d,J=0.5Hz,C-3 methyl), 7.90 (3H,s,$SCH_3$), 6.93 (1H,broad,N—H), 5.50 (2H,broad s,C-6 and C-7), 5.27 (2H,s,—$CH_2$—$CCl_3$), 3.85 (1H.d,J=0.5Hz,C-2), 2.6 (15H,m,aromatics).

c. 3-Methyl-4-methylthio-7-amino-$\Delta^2$-cephem-4-carboxylic acid, 2,2,2-trichloroethyl ester and its hydrochloride salt A mixture of the product from part (b) (12.0 g.) and 3.0 ml. of concentrated HCl in 180 ml. of acetone is stirred for 3 hours at 25° under nitrogen. The solvents are removed in vacuo and the residue is treated with acetone-ether to give the above mentioned product in the hydrochloride salt form as a powder (6.46 g.). Treatment of this salt with CHCl₃ and aqueous NaHCO₃ provides the desired product in the free base form, having pmr (DCCl₃) τ 8.17 (2H,broad s,—NH₂), 8.00 (3H,d,J=0.5Hz,C-3 methyl), 7.93 (3H,s,S—CH₃), 5.52 (1H,d,J=5Hz,C-7), 5.05, 5.30 (2H,q,J=12Hz,—CH₂—CCl₃), 4.72 (1H,d,J=5Hz,C-6), 3.60 (1H,d,J=0.5Hz,C-2).

d. 3-Methyl-4-methylthio-7-phenylacetamido-Δ²-cephem-4-carboxylic acid, 2,2,2-trichloroethyl ester To a stirred mixture of the hydrochloride salt (15 mmol.) from part (c) in 100 ml. of dry CH₂Cl₂ at 0° under nitrogen is added 4.3 ml. (31.6 mmol.) of triethylamine followed by 2.39 ml. (18.1 mmol.) of phenylacetyl chloride. The mixture is stirred at room temperature for 1.5 hours, and then washed twice with water, water at pH 7.6, and saturated aqueous NaCl. The CH₂Cl₂ layer is dried (Na₂SO₄) and evaporated in vacuo to give the desired product as a residue (7.42 g.) having: pmr (DCCl₃) τ 8.02 (3H,d,J=0.5Hz,C-3 methyl), 7.97 (3H,s,S—CH₃), 5.05, 5.28 (2H,q,J=13Hz,—CH₂—CCl₃), 4.70 (1H,d,J=5Hz,C-6), 4.47, 4.60 (1H,q,J=5Hz,J=8Hz,C-7), 3.67 (1H,d,J=0.5Hz,C-2); ir (CHCl₃) 1782, ~1762 (sh), and 1680 cm⁻¹; mass spectrum m/e 508 (M+).

e. 3-Methyl-4-methylthio-7-phenylacetamido-Δ²-cephem-4-carboxylic acid

A mixture of 0.517 mmol. of the product from part (d), 5.17 ml. of 0.1 N NaOH and 5 ml. of dioxane is stirred under N₂ at room temperature for 1 hour and then evaporated to dryness in vacuo to a residue which is taken up in water and washed repeatedly with ethyl acetate to remove neutral material. The aqueous layer (layered with ethyl acetate) is acidified to pH 2.0 and extracted with ethyl acetate (3 times). The combined extract is washed with water, dried (Na₂SO₄) and evaporated in vacuo to give the desired product as a residue (198 mg.) having pmr (DCCl₃) τ 8.03 (3H,d,J=0.5Hz,C-3 methyl), 7.93 (3H,s,SCH₃), 4.75 (1H,d,J=4Hz,C-6), 4.48, 4.62 (1H,q,J=4Hz,J=7Hz, C-7), 3.73 (1H,d,J=0.5Hz,C-2); ir (CHCl₃) 1775, 1742, and 1680 cm⁻¹.

EXAMPLE 2

3-[(Acetyloxy)methyl]-2-methylthio-7-phenylacetamido-Δ³-cephem-4-carboxylic acid a. 7-[(Triphenylmethyl)amino]-3-[(acetyloxy)methyl]-Δ³-cephem-4-carboxylic acid, t-butyl ester A mixture of 7-amino cephalosporanic acid t-butyl ester (30 mmol.), triphenylmethyl chloride (30 mmol.), and N,N-diisopropylethylamine (30 mmol.) in 150 ml. of dry CH₂Cl₂ is stirred at 25° under nitrogen for 4 hours. The reaction mixture is washed successively with water, dilute (Na₂SO₄) and evaporated in vacuo to a residue which is chromatographed on 400 g. of silica gel packed in CHCl₃. Elution with CHCl₃ provides 12.3 g. of the desired product as a residue.

b. 7-[(Triphenylmethyl)amino]-3-[(acetyloxy)methyl]-4-methylthio-Δ²-cephem-4-carboxylic, t-butyl ester To a stirred solution of the product from part (a) (5 mmol.) in 30 ml. of dry dimethoxyethane at −10° C under nitrogen is added 5 mmol. of potassium t-butoxide. The mixture is stirred for 2 minutes, and then methyl methanethiolsulfonate (5 mmol.) in 3 ml. of dimethoxyethane is added. The mixture is stirred at 0° for 1 hour and poured into pH 6.6 buffer-CHCl₃-ice. The CHCl₃ extract is washed with saturated NaCl, dried (Na₂SO₄), and evaporated to a residue, which is purified by dry column chromatography on a column of silica gel (2 × 24 inches) with CHCl₃ as solvent, to give 1.89 g. of the desired product as a foam having: pmr (DCCl₃) τ 8.57 (9H,s,t-butyl), 7.98, 7.92 (two 3H singlets,SCH₃,OAc), 6.97 (1H,broad d,N-H), 5.52 (1H,d,J=4Hz,C-6), 5.38 (1H,q,J=4Hz,J=9Hz,C-7), 5.20 (2H,broad s,C-3 methylene), 3.43 (1H,broad s,J~0.5Hz,C-2), and 2.67 (15H,m,aromatics).

c. 7-Amino-3-[(acetyloxy)methyl]-4-methylthio-Δ²-cephem-4-carboxylic acid,t-butyl ester (free base and hydrochloride salt)

A mixture of 1 mmol. of the product from part (b) and 0.17 ml. of concentrated HCl in 10 ml. of acetone is stirred at 25° for 3 hours under nitrogen. The mixture is evaporated to a residue whih is treated with 3 ml. of acetone and 50 ml. of ether to give a precipitate. The precipitate is washed with ether (3 × s) and dried in vacuo to give the above named product in the form of its hydrochloride salt (286 mg. of white powder). The hydrochloride salt (200 mg.) is dissolved in CHCl₃—H₂O, and dilute NaHCO₃ is added to adjust the pH to 7.2. After extracting, the CHCl₃ layer is washed with water, dried (Na₂SO₄), and evaporated in vacuo to give 153 mg. of the above mentioned product as a residue in its free base form. The free base has: pmr (DCCl₃) τ 8.48 (9H,s,t-butyl), 7.93 (6H,s,SCH₃,OAc), 6.43 (2H,broad band,NH₂), 5.17 (1H,d,J=5Hz,C-6), 5.13 (2H,broad singlet,C-3 methylene), 4.73 (1H,d,J=5Hz,C-7) and 3.17 (1H,d,J~0.5Hz,C-2).

d. 3-[(Acetyloxy)methyl]-4-methylthio-7-phenylacetamido-Δ²-cephem-4-carboxylic acid, t-butyl ester The hydrochloride salt from part (c), triethylamine and phenylacetyl chloride are reacted according to the procedure of example 1(d) to yield the titled compound.

e. 3-[(Acetyloxy)methyl]-2-methylthio-7-phenylacetamido-Δ³-cephem-4-carboxylic acid 30 mg. of the product from part (d) is placed into a dry flask. This is cooled in an ice bath and 2 ml. of trifluoroacetic acid are added. The solution is warmed to room temperature and stirred for 20 minutes. The reaction mixture is concentrated to dryness to obtain, as a residue, the tilted compound.

EXAMPLE 3

3-Methyl-2-methylthio-7-phenylacetamido-Δ³-cephem-4-carboxylic acid a. 7-[(Triphenylmethyl)amino]-3-methyl-Δ³-cephem-4-carboxylic acid, t-butyl ester By following the procedure for Example 2(a) but substituting 7-amino-3-methyl-Δ³-cephem-4-carboxylic acid t-butyl ester for 7-amino cephalosporanic acid t-butyl ester, the desired product is obtained as an amorphous residue having: pmr (DCCl₃) τ 7.93 (3H,s,C-3 methyl), 7.09, 6.72 (2H,q,J=18Hz,C-2), 5.80 (1H,d,J=5Hz,C-6), 5.30 (1H,broad band,C-7).

b. 7-[(Triphenylmethyl)amino]-3-methyl-4-methylthio-Δ²-cephem-4-carboxylic acid t-butyl ester By following the procedure of Example 2(b) but substituting the product from part (a) for the product from Example 2(a), the desired product is obtained as a residue having: pmr (DCCl$_3$) τ 8.57 (9H,s,t-butyl), 8.12 (3H,d,J=1Hz,C-3 methyl), 7.98 (3H,s,SCH$_3$), 5.48 (2H,broad s,C-6 and C-7), 3.93 (1H,d,J=1Hz,C-2), 2.67 (15H,m,aromatics); ir (CHCl$_3$) 1775 (β-lactam) and 1740 cm$^{-1}$ (ester); mass spectrum m/e 558 (M+).

c. 7-Amino-3-methyl-4-methylthio-Δ$^2$-cephem-4-carboxylic acid t-butyl ester (free base and hydrochloride salt)

By following the procedure of Example 2(c) but substituting the product from part (b) for the product from Example 2(b), the desired product, as its hydrochloride salt, is obtained as a powder. Treatment of this powder with CHCl$_3$-aqueous NaHCO$_3$ as desired in Example 2(c) provides the desired product in the free base form having: pmr (DCCl$_3$) τ]8.48 (9H,s,t-butyl), 8.03 (3H,d,J-1Hz,C-3 methyl), 7.97 (3H,s,SCH$_3$), 5.48 (1H,d,J=5Hz,C-6), 4.75 (1H,d,J=5Hz,C-7), and 3.65 (1H,d,J=1Hz,C-2).

d. 3-Methyl-4-methylthio-7-phenylacetamido-Δ$^2$-cephem-4-carboxylic acid, t-butyl ester The hydrochloride salt from part (c), triethylamine and phenylacetyl chloride are reacted according to the procedure of example 1(d) to yield the titled compound.

e. 3-Methyl-2-methylthio-7-phenylacetamido-Δ$^3$-cephem-4-carboxylic acid

The product from part (d) is reacted with trifluoroacetic acid according to the procedure of example 2(e) to yield the titled compound.

EXAMPLES 4–21

Following the procedure of examples 1 to 3 but employing the 7-amino-cephalosporanic acid ester of Col. I and the thiolating agent of Col. II one obtains the triphenylmethyl compound of Col. III.

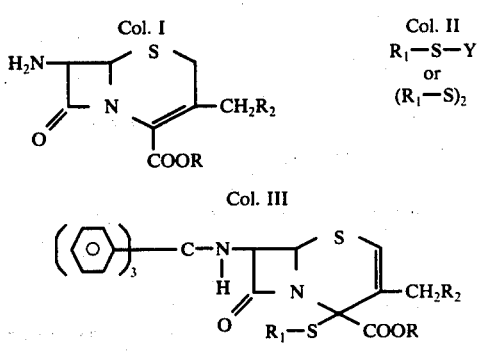

| Ex. | R | R$_2$ | thiolating agent | R$_1$ |
|---|---|---|---|---|
| 4 | —CH$_2$CCl$_3$ | —H | CH$_3$—S—S(=O)—CH$_3$ | —CH$_3$ |
| 5 | —CH$_2$CCl$_3$ | —OCCH$_3$ (O) | CH$_3$—S—S(=O)—CH$_3$ | —CH$_3$ |
| 6 | —CH$_2$CCl$_3$ | —H | (C$_2$H$_5$—S)$_2$ | —C$_2$H$_5$ |
| 7 | —CH$_3$ | —H | CH$_3$—S—S(=O)—CH$_3$ | —CH$_3$ |
| 8 | —CH$_3$ | —OCCH$_3$ (O) | (i-C$_3$H$_7$—S)$_2$ | —i-C$_3$H$_7$ |
| 9 | —C$_2$H$_5$ | —H | (t-C$_4$H$_9$—S)$_2$ | —t-C$_4$H$_9$ |
| 10 | —n-C$_4$H$_9$ | —OCCH$_3$ (O) | (CH$_3$—S)$_2$ | —CH$_3$ |
| 11 | —CH$_2$CCl$_3$ | —H | (Ph—S)$_2$ | Ph— |
| 12 | —CH$_2$CCl$_3$ | —OCCH$_3$ (O) | Ph—S—C(=O)—OCH$_3$ | Ph— |
| 13 | —CH(Ph)$_2$ | —H | CH$_3$—S—S(=O)—CH$_3$ | —CH$_3$ |
| 14 | —CH(Ph)$_2$ | —OCCH$_3$ (O) | (C$_2$H$_5$—S)$_2$ | —C$_2$H$_5$ |

-continued

| Ex. | R | $R_2$ | thiolating agent | $R_1$ |
|---|---|---|---|---|
| 15 | —CH—(C₆H₅)₂ | —H | (C₆H₅—S)₂ | —C₆H₅ |
| 16 | —CH₂—C₆H₄—OCH₃ | —H | CH₃—S(=O)(=O)—S—CH₃ | —CH₃ |
| 17 | —CH₂—C₆H₄—NO₂ | —OCCH₃ (O=) | (C₂H₅—S)₂ | —C₂H₅ |
| 18 | —CH₂—C₆H₄—NO₂ | —H | (n-C₃H₇—S)₂ | —n-C₃H₇ |
| 19 | —CH₂—C₆H₄—NO₂ | —OCCH₃ (O=) | (t-C₄H₉—S)₂ | —t-C₄H₉ |
| 20 | —C—(CH₃)₃ | —H | (C₆H₅—S)₂ | —C₆H₅ |
| 21 | —C—(CH₃)₃ | —OCCH₃ (O=) | C₆H₅—S—C(=O)—OCH₃ | —C₆H₅ |

The triphenylmethyl group of the products of examples 4 to 21 can be removed according to the procedure of example 1(c). The resulting 7-amino-4-thio substituted-cephalosporin esters can then be acylated with a compound of the formula

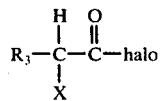

or an acid anhydride or mixed anhydride. The resulting 7-acyl-4-thio substituted-$\Delta^2$-cephalosporin esters wherein the esters is 2,2,2-trichloroethyl or lower alkyl other than t-butyl can be treated with base such as sodium hydroxide according to the procedure of example 1(e) to yield the 7-acyl-4-thio substituted-$\Delta^2$-cephalosporanic acid. The resulting 7-acyl-4-thio substituted-$\Delta^2$-cephalosporanic esters wherein the ester is p-nitrobenzyl are dissolved in a mixture of acetonitrile and water. The pH is adjusted to 8 by adding dilute sodium hydroxide, and 3 mmol. of sodium dithionite in 5 ml. of 1N sodium hydroxide is added. The mixture is then stirred and filtered, and the filtrate is layered with ethyl acetate and the pH adjusted to 2.5 to yield the 7-acyl-4-thio substituted-$\Delta^2$-cephalosporanic acid. The resulting 7-acyl-4-thio substituted-$\Delta^2$-cephalosporanic esters wherein the ester is t-butyl, p-methoxybenzyl, or diphenylmethyl can be treated with trifluoroacetic acid according to the procedure of example 2(e) to yield the 7-acyl-2-thio substituted-$\Delta^3$-cephem-4-carboxylic acid.

EXAMPLE 22

3-Methyl-4-methylthio-7-phenylacetamido 2-cephem-4-carboxylic acid a. 7-[(Methoxyphenylmethylene)amino]-3-methyl-$\Delta^3$-cephem-4-carboxylic acid, 2,2,2-trichloroethyl ester A mixture of 0.098 mol. of 7-amino desacetoxycephalosporanic acid, 2,2,2-trichloroethyl ester, 0.098 mol of trimethyl orthobenzoate and 50 mg. of p-toluenesulfonic acid monohydrate in 450 ml. of dry benzene is refluxed under $N_2$ for 5 hours during which time 300 ml. of benzene is removed by distillation, and fresh benzene is added to maintain the volume of the reaction mixture at 400 ml. The mixture is then diluted with benzene and washed sequentially with cold dilute $NaHCO_3$ at pH 7.6, cold dilute HCl at pH 2.0, and $H_2O$. It is then dried ($Na_2SO_4$) and evaporated to a residue which crystallizes from ether to give the desired product (28.5 g.). Repeated recrystallization gives a sample having m.p. 133°–135.5°.

Anal. Calc'd. for $C_{18}H_{17}N_2O_4SCl_3$: C, 46.62; H, 3.70; N, 6.04; Cl, 22.93. Found: C, 46.60; H, 3.63; N, 5.94; Cl, 23.20.

b. 7-[(Methoxyphenylmethylene)amino]-3-methyl-4-methylthio-$\Delta^2$-cephem-4-carboxylic acid, 2,2,2-trichloroethyl ester To a stirred solution of 0.062 mol. of N-cyclohexyl-N-isopropylamine in 150 ml. of dry dimethoxyethane under nitrogen at $-65°$ to $-70°$ is added 33.3 ml. of 2.2 M n-butyl lithium in hexane (0.067 mol.). This mixture is stirred for 10 minutes, and with the temperature at $-50°$ to $-60°$, the product from part (a) (0.062 mol.) in 150 ml. of dry dimethylformamide is added at a fast dropping rate. The mixture is stirred for 2 minutes after the addition, and then methyl methanethiolsulfonate (0.062 mol.) in 25 ml. of dry dimethoxyethane is added dropwise. Stirring is continued for 50 minutes at $-50°$ to $-60°$, and the mixture is poured into benzene-pH 6.6 buffer-ice. The benzene layer is washed with water three times, dried ($Na_2SO_4$) and evaporated in vacuo to a brown gum (27.9 g.). Dry column chromatography of this material on three columns of silica gel (2 × 25 inches) in the system hexane-ethyl acetate (17:3) provides the desired product as a residue (16.6 g.) having: pmr (DCCl₃) $\tau$ 8.00 (3H,d,J=0.5Hz,C-3 methyl), 7.83 (3H,s,SCH₃), 6.10 (3H,s,OCH₃), 5.17 (2H,s,—CH₂CCl₃), 5.02 (1H,d,J=5Hz,C-6), 4.72

(1H,d,J=5Hz,C-7), 3.45 (1H,d,J=0.5Hz,C-2), 2.4 (5H,m,aromatics).

c. 7-phenylacetamido-3-methyl-4methylthio-Δ²-cephem-4-carboxylic acid, 2,2,2-trichloroethyl ester A mixture of the product from part (b) (0.01 mol.), phenylacetyl chloride (0.02 mol.), and water (0.02 mol.) in 30 ml. of dichloromethane is stirred at 25° under nitrogen for 45 minutes. The mixture is diluted with $CH_2Cl_2$ and washed with cold aqueous $NaHCO_3$ at pH 7.5. The $CH_2Cl_2$ layer is washed with water, dried ($Na_2SO_4$), and evaporated in vacuo to a residue (7.56 g.), which is purified by dry column chromatography on silica gel columns (2 × 25 inches) in the system hexane-ethyl acetate (3:1). Final purification by preparative thin layer chromatography on ten 20 × 40 cm × 1 mm silica gel plates in the system hexane-ethyl acetate (1:1) provides the desired product as a residue (1.83 g.) having: pmr (DCCl₃) τ 8.02 (3H,d,J=0.5Hz,C-3 methyl), 7.97 (3H,s,S—CH₃), 4.70 (1H,d,J=5Hz,C-6), 4.47, 4.60 (1H,q,J=5Hz,J=8Hz,C-7), 3.67 (1H,d,J=0.5Hz,C-2); ir (CHCl₃) 1782, ~1762 (sh), and 1680 cm⁻¹.

d. 3-Methyl-4-methylthio-7-phenylacetamido ²-cephem-4-carboxylic acid

The product from part (c) is treated with sodium hydroxide according to the procedure of example 1(e) to yield the titled compound.

EXAMPLE 23

3-[(Acetyloxy)methyl]-2-methylthio-7-phenylacetamido-Δ²-cephem-4-carboxylic acid a. 7-[(Methoxyphenylmethylene)amino]-3-[(acetyloxy)methyl]-Δ³-cephem-4-carboxylic acid, t-butyl ester A mixture of 10 mmol. of 7-amino cephalosporanic acid t-butyl ester, 10 mmol. of trimethyl orthobenzoate, and 100 mg. of p-toluenesulfonic acid monohydrate in 100 ml. of dry benzene is refluxed under nitrogen for 6 hours during which time 15 ml. of benzene is removed by distillation. The reaction mixture is diluted with benzene and water, and the benzene layer is washed sequentially with cold dilute $NaHCO_3$ at pH 8, water, dilute HCl at pH 2.5, and water. The benzene layer is dried ($Na_2SO_4$), and evaporated to a residue which crystallizes from acetone-petroleum ether to give 2.43 g. of the desired product having m.p. 130°–134° (dec.).

b. 7[(Methoxyphenylmethylene)amino]-3-[(acetyloxy)methyl]-4-methylthio-Δ²-cephem-4-carboxylic acid, t-butyl ester To a stirred solution of N-cyclohexylisopropylamine (0.5 mmol.) in 3 ml. of dry dimethoxyethane at −70° under nitrogen is added 0.3 ml. of 2.0M n-butyl lithium in hexane. The mixture is stirred at −70° for 10 minutes, and 0.5 mmol. of the product from part (a) in 3 ml. of dry dimethylformamide is added dropwise and rapidly. The mixture is stirred for 2 minutes, and methyl methanethiosulfonate (0.5 mmol.) in 0.5 ml. of dimethylformamide is added. The mixture is stirred at −65° to −55° for 40 minutes and poured into pH 6.6 buffer-ice-benzene. The benzene layer is washed repeatedly with water, dried ($Na_2SO_4$), and evaporated to a residue. Preparative thin layer chromatography on silica gel in CHCl₃ provides 86 mg. of the desired product having: pmr (DCCL₃) τ 8.50 (9H,s,t-butyl), 7.93, 7.88 (two 3H singlets,SCH₃ and OAc), 6.10 (3H,s,OCH₃), 4.98 (1H,d,J=5Hz,C-6), 4.78 (1H,d,J=5Hz,C-7), 3.05 (1H,s,C-2), 2.0–2.7 (5H,m,aromatics); ir (CHCl₃) 1770 (β-lactam), 1735 (esters), and 1650 cm⁻¹ (C=N); mass spectrum m/e 492 (M+).

c. 7-Phenylacetamido-3-[(acetyloxy)methyl]-4-methylthio-Δ²-cephem-4-carboxylic acid, t-butyl ester To a mixture of the product from part (b) (10 mmol.) in 40 ml. of $CH_2Cl_2$ is added phenylacetyl chloride (20 mmol.) followed by 20 mmol. of water. The mixture is stirred at 25° under nitrogen for 18 hours and diluted with $CH_2Cl_2$ and water. After extracting, the $CH_2Cl_2$ layer is washed with dilute aqueous $NaHCO_3$ at pH 8 and then water. It is then dried ($Na_2SO_4$) and evaporated to a residue which is chromatographed on silica gel to give the desired product as an amorphous solid.

d. 3-[(Acetyloxy)methyl]-2-methylthio-7-phenylacetamido-Δ³-cephem-4-carboxylic acid The product from part (c) is treated with trifluoroacetic acid according to the procedure of example 2(e) to yield the titled compound.

EXAMPLES 24–41

Following the procedure of examples 22 and 23 but employing the 7-amino-Δ³-cephalosporanic ester of Col. I, the ortho ester of Col. II, and the thiolating agent of Col. III, one obtains the compound of Col. IV.

Col. I

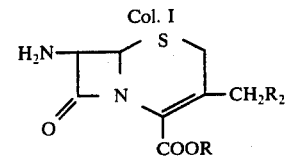

Col. II

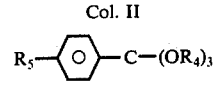

Col. III
$R_1—S—Y$
or
$(R_1—S)_2$

Col. IV

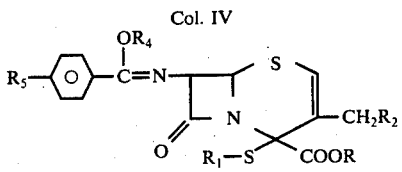

| Ex. | R | R₂ | thiolating agent | R₁ | R₄ | R₅ |
|---|---|---|---|---|---|---|
| 24 | —CH₂CCl₃ | —H | (C₂H₅—S)₂ | —C₂H₅ | —CH₃ | —H |
| 25 | —CH₂CCl₃ | —OCCH₃ (O) | CH₃—S—S—CH₃ (O) | —CH₃ | —CH₃ | —H |

-continued

| Ex. | R | $R_2$ | thiolating agent | $R_1$ | $R_4$ | $R_5$ |
|---|---|---|---|---|---|---|
| 26 | $-CH_2CCl_3$ | $-OCCH_3$ (O) | $(\text{Ph}-S)_2$ | $\text{Ph}-$ | $-C_2H_5$ | $-H$ |
| 27 | $-CH_3$ | $-H$ | $(n-C_3H_7-S)_2$ | $-n-C_3H_7$ | $-C_2H_5$ | $-H$ |
| 28 | $-CH_3$ | $-OCCH_3$ (O) | $\text{Ph}-S-C(O)-OCH_3$ | $\text{Ph}-$ | $-CH_3$ | $-CH_3$ |
| 29 | $-C_2H_5$ | $-H$ | $(t-C_4H_9-S)_2$ | $-t-C_4H_9$ | $-CH_3$ | $-OCH_3$ |
| 30 | $-C_2H_5$ | $-OCCH_3$ (O) | $C_2H_5-S-Cl$ | $-C_2H_5$ | $-C_2H_5$ | $-OCH_3$ |
| 31 | $-n-C_3H_7$ | $-H$ | $CH_3-S-S(O)-CH_3$ | $-CH_3$ | $-CH_3$ | $-CH_3$ |
| 32 | $-CH_2-\text{C}_6\text{H}_4-OCH_3$ | $-H$ | $(C_2H_5-S)_2$ | $-C_2H_5$ | $-CH_3$ | $-H$ |
| 33 | $-CH_2-\text{C}_6\text{H}_4-OCH_3$ | $-OCCH_3$ (O) | $(\text{Ph}-S)_2$ | $\text{Ph}-$ | $-CH_3$ | $-OCH_3$ |
| 34 | $-CH_2-\text{C}_6\text{H}_4-NO_2$ | $-H$ | $CH_3-S-S(O)-CH_3$ | $-CH_3$ | $-C_2H_5$ | $-H$ |
| 35 | $-CH_2-\text{C}_6\text{H}_4-NO_2$ | $-OCCH_3$ (O) | $(n-C_3H_7-S)_2$ | $-n-C_3H_7$ | $-C_2H_5$ | $-CH_3$ |
| 36 | $-CH(\text{Ph})_2$ | $-H$ | $CH_3-S-S(O)-CH_3$ | $-CH_3$ | $-C_2H_5$ | $-H$ |
| 37 | $-CH(\text{Ph})_2$ | $-OCCH_3$ (O) | $(C_2H_5-S)_2$ | $-C_2H_5$ | $-CH_3$ | $-OCH_3$ |
| 38 | $-CH(\text{Ph})_2$ | $-OCCH_3$ (O) | $\text{Ph}-S-C(O)-OCH_3$ | $\text{Ph}-$ | $-CH_3$ | $-CH_3$ |
| 39 | $-C(CH_3)_3$ | $-OCCH_3$ (O) | $CH_3-S-S(O)-CH_3$ | $-CH_3$ | $-CH_3$ | $-H$ |
| 40 | $-C(CH_3)_3$ | $-H$ | $(i-C_3H_7-S)_2$ | $-i-C_3H_7$ | $-C_2H_5$ | $-OCH_3$ |
| 41 | $-C(CH_3)_3$ | $-OCCH_3$ (O) | $(\text{Ph}-S)_2$ | $\text{Ph}-$ | $-CH_3$ | $-CH_3$ |

The compound of Col. IV. of examples 24 to 41 can be acylated according to the procedure of examples 22(c) with various acyl halides of the formula

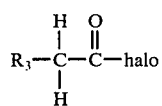

to prepare various 7-acyl-4-thio substituted-Δ²-cephalosporin esters. The resulting 2,2,2-trichloroethyl or lower alkyl esters (other than t-butyl) can be treated with base such as sodium hydroxide according to the procedure of example 1(e) and the p-nitrobenzyl esters can be treated with sodium dithionite to yield the 7-acyl-4-thio substituted-Δ²-cephem-4-carboxylic acid. The t-butyl, p-methoxybenzyl, or diphenylmethyl esters can be treated with trifluoroacetic acid according to the procedure of example 2(e) to yield the 7-acyl-2-thio substituted-Δ³-cephem-4-carboxylic acids.

What is claimed is:

1. A compound of the formula:

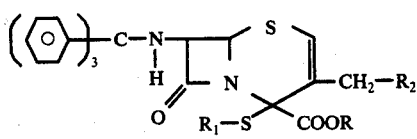
wherein R is lower alkyl, 2,2,2-trichloroethyl, p-methoxybenzyl, p-nitrobenzyl, or diphenylmethyl; $R_1$ is lower alkyl or phenyl; and $R_2$ is hydrogen or acetoxy.
2. The compound of claim 1 wherein $R_1$ is methyl.
3. The compound of claim 2 wherein R is t-butyl.
4. The compound of claim 2 wherein R is 2,2,2-trichloroethyl.
* * * * *

UNITED STATES PATENT OFFICE
CERTIFICATE OF CORRECTION

Patent No. 4,039,534          Dated August 2, 1977

Inventor(s) William A. Slusarchyk & Christopher M. Cimarusti

It is certified that error appears in the above-identified patent and that said Letters Patent are hereby corrected as shown below:

Col. 4 in the formula, add "$OCH_3$" where indicated:

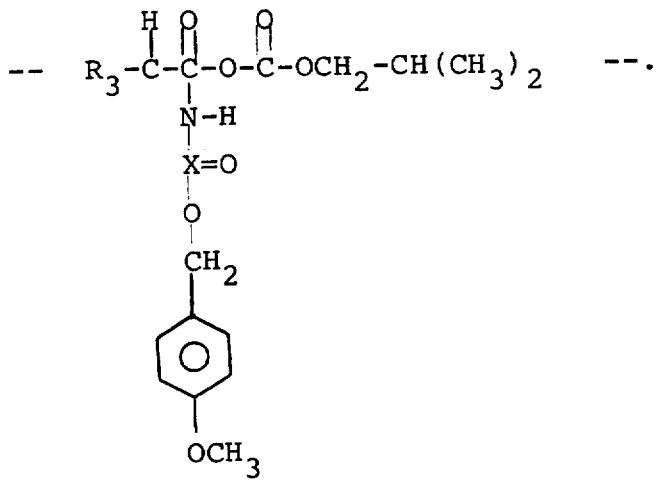

Col. 6, line 60 "(1H.d,J=0.5Hz,C-2)" should read:
-- (1H,d,J=0.5Hz,C-2) --.

Col. 9, line 17, "$NaHCO_3$ as desired" should read:
-- $NaHCO_3$ as described --.

Col. 9, line 19, "pmr($DCCL_3$) τ]" should read: -- pmr($DCCL_3$) τ -

Col. 9, line 20, "32 1Hz,C-3 methyl)," should read:
-- =1Hz,C-3 methyl), --.

Col. 11, line 61 & 62, in Example 22, should read:
-- 3-Methyl-4-methylthio-7-phenylacetamido $\Delta^2$-cepham-4-carboxylic acid --.

UNITED STATES PATENT OFFICE
CERTIFICATE OF CORRECTION

Patent No. 4,039,534     Dated August 2, 1977

Inventor(s) William A. Slusarcyk & Christopher M. Cimarusti

It is certified that error appears in the above-identified patent and that said Letters Patent are hereby corrected as shown below:

Col. 13 in point d. of Example 22, insert the symbol "$\Delta$" where indicated below:
-- d. 3-Methyl-4-methylthio-7-phenylacetamido $\Delta^2$-cephem-4-carboxylic acid --.

Signed and Sealed this

Sixth Day of December 1977

[SEAL]

Attest:

RUTH C. MASON
*Attesting Officer*

LUTRELLE F. PARKER
*Acting Commissioner of Patents and Trademarks*